United States Patent
Frismark et al.

(10) Patent No.: US 6,703,010 B1
(45) Date of Patent: Mar. 9, 2004

(54) SPRAY CONTAINING AMPHOTERIC MATERIAL TO REDUCE MALODORS

(76) Inventors: Jan Frismark, Kyrkbyn 3, S-24036, Stehag (SE); Arne Lund Kvernheim, Bakkegårdsveien 20, N-1450 Nesoddtangen (NO); Ole Widar Saastad, Sarpsborggata 14c, N-0468 Oslo (NO); Ronnie Thomasson, Box 1501, S-22101 Lund (SE); Børre Bengt Ulrichsen, Holmenkollveien 33B, N-0376 Oslo (NO); Fred Archer, Prost Hallingsvei 12, N-0666 Oslo (NO)

( * ) Notice: Subject to any disclaimer, the term of this patent is extended or adjusted under 35 U.S.C. 154(b) by 0 days.

(21) Appl. No.: 09/831,936

(22) PCT Filed: Nov. 15, 1999

(86) PCT No.: PCT/IB99/01835

§ 371 (c)(1),
(2), (4) Date: May 14, 2001

(87) PCT Pub. No.: WO00/29039

PCT Pub. Date: May 25, 2000

(30) Foreign Application Priority Data

| Nov. 14, 1998 | (GB) | 9824922 |
| Nov. 14, 1998 | (GB) | 9824924 |
| Jul. 15, 1999 | (GB) | 9916503 |
| Jul. 15, 1999 | (GB) | 9916506 |
| Sep. 15, 1999 | (GB) | 9921747 |

(51) Int. Cl.[7] .............. A61L 9/01; A61L 9/14; A61L 9/04; A61K 7/035

(52) U.S. Cl. ............ 424/76.1; 424/76.2; 424/46; 424/43; 424/45; 424/69

(58) Field of Search ............ 424/76.1, 46, 69, 424/76.2, 43, 45

(56) References Cited

U.S. PATENT DOCUMENTS 4,902,434 A * 2/1990 Dickerson ............ 252/8.6
4,995,556 A * 2/1991 Arnold, III ........... 239/57

* cited by examiner

*Primary Examiner*—Thurman K. Page
*Assistant Examiner*—Blessing Fubara
(74) *Attorney, Agent, or Firm*—The Weintraub Group, P.L.C.

(57) ABSTRACT

Powder compositions usable to reduce malodours, and powder formulations from which can be made aqueous spray compositions usable to reduce malodours, each comprise, as a major ingredient, amphoteric material, for example sodium bicarbonate, potassium bicarbonate, or zinc oxide, together with one or more minor ingredients, in particular a drying agent, for example sodium sulphate. Other minor ingredients may be an ammonia-odour/sulphide-odour remover, for example ferrous sulphate or zinc sulphate, and an adsorbent, for example zeolite, in the case of a powder formulation; or a filler, for example potassium chloride, or an organic complexing agent, for example cyclodextrin, or a surfactant, in the case of a stock formulation.

8 Claims, No Drawings

SPRAY CONTAINING AMPHOTERIC MATERIAL TO REDUCE MALODORS

This invention is concerned with compositions, and relates in particular to powder compositions and spray compositions that can be employed to reduce or even remove objectionable smells.

Undesirable odours are a nuisance in many situations; unpleasant smells may at best put people off their work, while at worst they may actually make them feel—and perhaps be—physically sick. Because the human nose can detect smells at active-ingredient levels as low as one part per billion (1 ppb), far below what most analysing equipment can detect, it is difficult to document such reductions by instrumental methods, and there is a serious problem in reducing or removing smells so as to improve the environment.

The molecules of substances that cause smells can range widely in both size and chemical nature. Some are large, and possibly filterable; others are not only too small to be removed that way, they are so small that they can stay suspended in the air for long periods. Some are hydrophobic (and so usually water-insoluble), such as the paraffins/hydrocarbons/mineral oils like diesel and gasoline and many fat soluble esters used as flavour ingredients, while others are hydrophilic (and so usually water-soluble), such as organic acids like butyric acid, (the "rancid butter" smell) and many inorganic compounds like ammonia and hydrogen sulphide. The hydrophilic smell-forming materials can also be subdivided into those that are alkaline, such as ammonia and amines (which often smell fishy), those that are neutral, such as the alcohols (some of the $C_{3-6}$ alcohols smell quite disgusting) and mercaptans giving odours typically related to decay of vegetables like cabbage, and those that are acidic, such as the butyric acid found in sour milk and butter products and the hydrogen sulphide found in rotten organic matter (the smell of a bad egg is mostly due to hydrogen sulphide).

In the past many attempts have been made to produce an all-purpose deodorizer, using many combinations of odour-combatting and masking chemicals. Some have been more successful than others, but none has proved truly victorious in the fight against smells. The present invention suggests a novel way of utilising some of the known chemicals, and even a novel combination of some of those chemicals, that seems to be significantly and perhaps surprisingly more effective than those presently available in the marketplace. This novel utilisation is based upon the use of amphoteric material, in particular sodium bicarbonate, in the form of an aqueous spray.

Amphoteric material has both acidic and basic properties, and so can form salts or adducts with both bases and acids. A well-known amphoteric compound is sodium bicarbonate—$NaHCO_3$—also known as baking powder.

For many years it has been known that baking powder can be used to remove certain smells from refrigerators or on a surface by spreading it over that surface, leaving it to absorb the smell (no doubt at least partially by reacting chemically with the smell), and then wiping it up. However its acceptance has largely been limited to odour neutralisation in smaller household applications. This is probably due to its rather slow activity in odour removal because it has very limited capacity for most sulphides and mercaptans. It is also very sensitive to moisture; a 5% moisture content can often reduce the neutralisation capacity in respect of some odour molecules by more than 50%. A higher moisture content results in lumps forming which will reduce dramatically the active surface area and thus the neutralising capability. Furthermore, the consistency of baking powder is often such that it will create a very objectionable dust (irritating to breathe in and to have in skin contact). When such dust settles, it clings strongly to most surfaces and is even very difficult to remove by vacuum cleaning. These functional limitations may be the main reasons for its rather limited application and acceptance in the market over the years even though sodium bicarbonate has often been used as a relatively minor ingredient or filler substance in more complex deodorizing compositions.

U.S. Pat. No. 5,303,676 and U.S. Pat. No. 5,421,291 disclose an animal litter composition in which sodium bicarbonate or potassium bicarbonate is a minor ingredient. The composition comprises 1) a particulate, water-absorbent, clayey component, e.g., sodium bentonite, containing at least one water-swellable clay mineral, e.g., montmorillonite; and 2) a solid particulate deodorizing additive component comprising sodium bicarbonate or potassium bicarbonate, the particles of which are substantially coated with a mineral oil, mixed with a powdered siliceous material, e.g., expanded perlite, having a bulk density significantly lower than the density of sodium bicarbonate or potassium bicarbonate, the coated particles of sodium bicarbonate or potassium bicarbonate being stably adhered to and agglomerated with the particles of the. siliceous material. The animal litter composition contains about 80–98 weight %, preferably about 90–95 weight %, of clayey component provided by the sodium bentonite and about 2–20 weight %, preferably about 5–10 weight %, of deodorising additive component, provided largely by the bicarbonate. The composition may also optionally contain about 0.1 to 1 weight % of zinc oxide to exert a bactericidal action on the waste products in the litter.

GB-A-1356343 discloses a toilet-bowl-sanitising, foam-forming composition which may contain odour-improving additives or deodourising additives. In a particular example, three spray preparations are described. The preparations comprise 17; 23.40 or 22.20 parts of surface active agent(s), 0.1; 0.1 or 0.6 parts of disinfectant or germicide and 1 part alcohol, mixed with an aqueous solution comprising 80.35; 73.95 or 75.15 parts of water, and 1.5 parts of perfume. In a further example, a powder or granulate preparation is described comprising either 40 parts sodium carbonate and 40 parts citric acid, or 30 parts sodium carbonate and 50 parts sodium bisulphate, together with, in each case, 20 parts sodium lauryl sulphate and 0.3 parts fatty alcohol.

WO-A-98/27261 describes an animal care system desirably including animal litter with reduced malodour impression comprising solid moisture-absorbing material and effective amounts of both odour-absorbing material, preferably cyclodextrin or derivative thereof, and material for reducing the formation of malodour, e.g., antibacterial and/or urease inhibitor, preferably water-soluble metallic salt such as zinc salt. Behaviour control products are also provided including animal repellent and attractant products, preferably in spray containers, and freshening and cleaning products, also especially in spray containers, and, preferably, in association with instructions for using the products to carry out a method of animal control in which the animal litter is refreshed as needed, and areas are treated with repellent and attractant products to influence the animals to avoid certain areas and frequent other areas, and products for cleaning areas where accidents occur and discouraging the animal from returning to those areas.

According to one aspect of the present invention, there is provided a stock formulation useful in the preparation of a spray composition, the formulation comprising, as a major ingredient, amphoteric material and being dispersible in liquid to produce a spray composition containing by weight a relatively small proportion of the formulation in-a relatively large proportion of liquid.

The amphoteric material is preferably inorganic material since, as compared with organic materials, inorganic materials are less susceptible to degradation, especially microbiological degradation over time, i.e. inorganic materials tend to be more stable. The inorganic material may be a salt, particularly sodium bicarbonate or potassium bicarbonate. Another advantage is that such salts are often more readily dissolved in water to create a spray liquid than are many organic substances.

Most advantageously, the formulation is in the form of a powder.

By "major" herein is meant, on the basis of a percentage by weight of the entire formulation, occurring in at least twice the percentage of any other individual ingredient of the formulation or in about 50% or more.

Very preferably, the amphoteric material is uncoated. By "uncoated" herein is meant not coated with any substance which significantly reduces that active surface area of the particles of amphoteric material available for reaction with gaseous odours. In particular, the formulation and the spray composition should be substantially free of oily matter.

We have found that if sodium bicarbonate—or, indeed, certain other amphoteric compounds—is used not as a minor ingredient of a make-up formulation (from which there is made the desired "use" composition) but as a major one, and, optionally, when the formulation is a powder, is combined with a significant proportion of drying agent, then this provides a stock formulation from which an extremely efficient deodorising aqueous spray composition, particularly an aerosol spray composition, can be made.

This spray composition can be used within an area or on a surface where there is a smell (if on a surface it can be allowed to stand for a time to absorb or neutralise that smell). This astonishing effect of an amphoteric compound dissolved in water and applied/distributed in an aerosol spray is indeed surprising. Sodium bicarbonate applied as a dry powder for odour absorption is extremely moisture sensitive. Only some 5% increase in moisture content will often reduce the capacity for neutralisation of some odour molecules by more than 50%. Further exposure to moisture can cause lump formation, with rather drastic capacity reduction as a consequence. It is, however, known that sodium bicarbonate dissolved in water can have some odour neutralising effect, for example it can be used as a mouthwash or for soaking dirty diapers. This effect is most likely attributable to acid/base reaction and neutralisation processes but possibly also to weak adsorption effects of remaining active material when the washing process is completed. Only very small amounts of active material can be distributed in an aerosol spray. This makes it less obvious to use sodium bicarbonate in a spray composition for effective odour neutralisation. This is probably the reason why no-one has previously thought of applying an amphoteric compound, e.g. sodium bicarbonate, as the main active ingredient in an aqueous spray for in-air odour neutralisation.

The invention also provides a spray composition made by dispersing, preferably dissolving, the relatively small proportion of the stock formulation in the relatively large amount of liquid.

The stock formulations of the invention are to be used in the preparation of spray deodorizing compositions. This preparation involves dispersing the formulation, and preferably actually dissolving it, in water so that there is produced a suitable spray composition. More is said about this hereinafter.

Advantageously, the stock formulations are alkaline, i.e. have a pH higher than 7 when dissolved in water. A major advantage is that very many decomposition products of organic matter resulting in odour are acidic and therefore tend to be neutralised by an alkaline composition applied to them. Moreover, a majority of the malodours that people most object to in their daily environment, such as in their homes, are acidic.

The stock formulations comprise as a major ingredient amphoteric material (in the form of one or more amphoteric compounds), and, optionally as a significant other ingredient, a drying agent. The percentage of amphoteric material is very preferably at least 55%. One particularly-preferred formulation contains 60% amphoteric material. By "a significant other" is meant that the amount of the drying agent is not small but equally is not so large that it could be thought of as the major ingredient. On the same percentage basis, there is desirably about 5% or more, sometimes at least 15%, and in some cases at least 25%, of the drying agent. Two formulations contain about 30% drying agent. A suitable drying agent is sodium sulphate, possibly with magnesium sulphate; another possible material for this purpose is potassium sulphate.

The invention's stock formulations comprise amphoteric material as one major ingredient. The amphoteric compound of choice is sodium bicarbonate, but another possible such compound is potassium bicarbonate.

The invention's spray composition can also include a preservant (otherwise known as a "preservative") to prevent microbiological growth. Such preservant, which is not necessary in the dry stock formulation (though it can be included therein), is preferably used in an amount of from about 7 ppm (0.0007%) to about 1 wt. % of the spray composition. Typical preservants are water water-soluble parabens usable in a total amount of about 0.5 wt. %, or sodium salts thereof. In other cases, an isothiazolinone material, for example "Kathon CG", (Trade Mark) can be used, in an amount of from about 7 ppm to about 20 ppm by weight to achieve compatibility with other ingredients of the spray composition. Another peservant which can be used is "SUTTOCIDE A" which is an hydroxymethylamine derivative.

The stock formulations of the invention are dispersible, and preferably soluble, in water, to produce a spray composition containing by weight a relatively small proportion of the formulation in a relatively large amount of water. The water may contain small amounts of co-solvents or droplet-size modifiers and these are typically surfactants such as lauryl sulphate (which may be added, in proportions of preferably a maximum of about 5 wt %, to alter droplet surface activities or to modify the dissolving capability in respect of specific odour compounds). Although notionally "dispersible" includes possibilities other than being soluble, the latter is very much preferred (and indeed the preferred materials are water-soluble to the extent required).

The formulations are dispersible/soluble in water to produce an aqueous spray composition—that is to say, a composition which is to be used in a manner in which it is sprayed around, either into the air of the area/volume to be treated or onto a surface to be treated (or adjacent the area/volume to be treated). If the spray composition is to be used to treat a space, it is advantageously in the form of an aerosol (in other words, atomized or finely divided spray), so that the spray droplets float in the atmosphere in the space. The composition is to contain by weight a relatively small proportion of the formulation in a relatively large amount of water. In this context "relatively small" means less than 10 wt %, possibly less than 5 wt %, and preferably about 1 wt %. Indeed, a preferred spray composition contains 1 wt %, of the stock formulation and 99 wt % water. This large proportion of water may seem odd, considering that it is the formulation's ingredients which are supposed to be dealing with the smells, but in fact it is not so odd. As noted hereinbefore, many smells are hydrophilic substances, and they will readily be adsorbed to the small droplets floating in air (due to the large total surface area of the droplets) and then be dissolved therein. Once they are dissolved, they can be more efficiently neutralised by the formulation's ingredients that are also dissolved in the droplets.

The surface area of droplets in a given volume of air will be the first and limiting step in the odour-removing process. The odour molecules must diffuse through air and find a droplet before the adsorption and subsequent dissolving steps can take place. The fineness of the spray droplets will thus be important for odour molecules to find a droplet. The concentration of the odour-removing constituents dissolved in water is therefore not thought to be critical as long as the concentration is at 1% or above.

The invention's stock formulations contain amphoteric material and optionally a drying agent and perhaps a preservant. They can also include relatively small amounts of one or more other materials to enhance ionic strength, add density, add solvating power and change (normally reduce) liquid surface tension. Typical such other materials are pH-neutral inorganic salts, such as potassium chloride and magnesium sulphate, or surfactants such as alcohol or detergents. The preferred quantities for these, when in dry form, are less than 10 wt %, and most preferably around 5 wt %. It is believed that the use of a surfactant, whether an amphoteric surfactant, such as Miranol Ultra, an anionic surfactant, such as lauryl sulphate, or a non-ionic surfactant, such as Brij 35 or Tween 40, or a cationic surfactant, will solubilize hydrophobic odour components and may also alter the surface tension of the liquid. Reducing the liquid surface tension may increase the fineness of the spray droplets.

Formulations may consist of about 60% amphoteric agent (sodium bicarbonate), about 35% drying agent (sodium sulphate+magnesium sulphate) and about 5% to about 10% filler (magnesium sulphate+potassium chloride); or about 60% amphoteric agent (sodium bicarbonate), about 10% drying agent and filler (magnesium sulphate) and about 30% organic completing agent (cyclodextrin)—this formulation being particularly suited to removing odours from textiles; or about 90% amphoteric agent (sodium bicarbonate), about 2% to about 4% drying agent (sodium sulphate+magnesium sulphate), about 2% to about 4% (magnesium sulphate+potassium chloride), and about 4% surfactant (Lauryl sulphate+Miranol Ultra+Brij 35+Tween 40)—this formulation being particularly suitable in removing odours from compost.

It is an important advantage of this invention, compared with many competitive products on the market, that the spray can be used without any masking agent, such as a perfume. Many individuals react negatively to such masking compounds by showing an allergic response.

The stock formulations of the invention can be made by simply mixing the ingredients in a screw mill, and this needs no further discussion at this point.

The invention provides a stock formulation useful in the preparation of a spray deodourizing composition, and it also provides such a spray composition (which can made simply by dispersing or indeed dissolving a relatively small proportion of the formulation in a relatively large amount of water). The invention's spray compositions can be used to remove smells both from the air within any area/volume and also from almost any kind of surface. Thus, for example, they can be sprayed into a room to remove smells from the air therein, or they can be sprayed directly onto a garment, a carpet or other soft-furnishings—curtains, sofas and the like—and any powdery residue (from the dissolved substances) later brushed/vacuumed off. No stains are left on the treated materials. Remaining substances left on glass or shiny surfaces treated are easily removed by normal washing/cleaning operations.

In a second aspect, the invention provides a method of interacting with gas at a location, in which an aqueous amphoteric composition is sprayed, preferably as an aerosol, at the location.

Most preferably the amphoteric composition includes sodium bicarbonate as the amphoteric material, and most conveniently is one of those compositions according to the present invention.

The toxicity level of the present preferred spray composition has been kept so low that no harm or irritation should come to users whether by inhalation or contact with the skin, even with extensive daily use. The alkaline nature of the stock formulation and spray composition however (pH 8.5 in water) makes the use of droplet inhalation protection and skin protection advisable for extensive use. The ingredients are used to a large extent in food products or as additives to farming soil. The composition neutralizes a number of materials that, in addition to generating odours, may cause allergic reactions. Moreover, the composition should not react chemically or otherwise damage constructional material, textiles, plastics, or the like.

The preferred spray composition is particularly useful in odour neutralisation work after fires, in forensic cases and the like. Trials have shown that an immediate reduction of odour level can be obtained by a simple water aerosol spray producing a fog in the ambient atmosphere. However, a residual odour always prevailed, as the human nose can detect odours down to very low levels, and the odour level normally increased once the odour-neutralising effect of the moisture particles ceased. On the other hand, with the preferred spray composition of the present invention, a chemical reaction with the odour molecules normally took place irreversibly. Although in very minute amounts, the spray composition spray also left some active material on surfaces (such as fabric, wood, concrete and the like) after spraying, so that not only the airborne odour molecules, but possibly also those adsorbed to those surfaces, were neutralised.

The spray composition is usable for odour neutralisation on the human body, particularly for wound odour neutralisation in hospital. For those purposes, the composition is advantageously isotonic, i.e. has the same osmotic potential as body fluids, whereby it can appropriately be applied on and around wounds.

According to a third aspect of the present invention, there is provided a powder composition comprising as a major ingredient uncoated amphoteric material together with relatively minor amounts of one or more of an alkaline- and/or sulphide-remover, an adsorbant, and a drying agent.

The composition is intended for interacting with gas, which is why it is essential that it is uncoated (as hereinbefore defined), and in particular that it is substantially free of oily matter.

According to a fourth aspect of the present invention, there is provided a powder composition constituting a consumer end product and comprising as a major ingredient amphoteric material together with relatively minor amounts of one or more of an alkaline- and/or sulphide-remover, an adsorbant, and a drying agent.

We have found that if sodium bicarbonate—or, indeed, certain other amphoteric compounds—is used not as a minor ingredient but as a major one, and if it is used in combination with relatively minor amounts of one or more of an alkali- and/or sulphide-remover (such as iron sulphate), an adsorbant (such as an amorphous mineral, e.g. silica, or a zeolite), and preferably a drying agent (such as sodium sulphate), there can be produced an extremely effective, deodourizing, dry, powder composition that can be spread onto a surface where there is a smell (either on the surface or in the air adjacent that surface), allowed to stand for a time to absorb or neutralise that smell, and then wiped off, taking the smell with it.

The powder compositions of the invention contain as a major (as hereinbefore defined, though in relation to the powder formulation) ingredient amphoteric material (in the form of one or more amphoteric compounds) together with relatively minor amounts of one or more other substances. Particularly-preferred compositions contain about 85% amphoteric material. By "relatively minor" is meant, on the same percentage basis, at least some of the material, but not more than 15%, and preferably not more than 10%. Particularly-preferred compositions contain about 3% to about 5% ammonia- and sulphide-remover, about 5% total adsorbant, and about 7% drying agent.

Examples of such particularly preferred compositions are by weight, about 85% sodium bicarbonate, about 3% to about 5% ferrous sulphate, about 7% sodium sulphate and about 5% zeolite; about 85% sodium bicarbonate, about 3% to about 5% zinc sulphate, about 7% sodium sulphate and about 5% zeolite; and about 50% sodium bicarbonate, about 35% zinc oxide, about 3% to about 5% ferrous sulphate, about 7% sodium sulphate and about 5% zeolite.

The invention's powder compositions contain amphoteric material as their major ingredient. Again, it is particularly advantageous for the amphoteric material to be inorganic, such as a salt, for example sodium bicarbonate or potassium bicarbonate. The amphoteric compound of choice is sodium bicarbonate. Another possible such compound is zinc oxide.

As minor ingredients, the powder compositions of the invention contain one or more of an alkaline-odour and/or sulphide-odour remover, an adsorbant, and—and preferably—a drying agent. The alkaline-odour and/or sulphide-odour remover is most conveniently iron sulphate (heptahydrate) (typically that material available from SvedaKjemi AS in Norway as "FERROMEL"). Another possible material can be zinc sulphate. The adsorbant is advantageously insoluble in water and may be one or both of an amorphous silica or a zeolite (typically the amorphous silica available from SvedaKjemi AS in Norway and the zeolite available from Keramika in Slovakia as "CLINOPTILOLITE"), and the drying agent is conveniently sodium sulphate available from SvedaKjemi AS in Norway, but another possible compound can be potassium sulphate.

Again, no masking agent, such as a perfume, need be added.

Bulk densities and particle sizes of the ingredients of the powder composition are chosen to allow proper mixing, to avoid component segregation, to avoid extensive dust problems when used, and to give good storage properties. Typically, bulk density should be in the 1–3 g/cm$^3$ range, and the particle size in the 0.1–1.0 mm range.

The powder compositions of the invention can be made by simply mixing the ingredients, and this needs no further discussion at this point, save perhaps to note that to achieve a powder either the constituents should themselves already all be in a powder state or the mixture should be made in some appropriate mixing and pulverising apparatus, such as a screw mill.

According to a fifth aspect of the present invention, there is provided in combination, a container of porous, and/or permeable material, and a powder composition according to the invention and in said container.

According to a sixth aspect of the present invention there is provided a method of neutralising odours, in which a powder composition according to the invention is applied to the source of the odour.

According to a seventh aspect of the present invention, there is provided a method of neutralising odours, in which there is applied to the source of the odour a powder composition comprising as a major ingredient amphoteric material together with relatively minor amounts of one or more of an alkaline- and/or sulphide-remover, an adsorbant, and a drying agent.

It is particularly advantageous if a synergistic effect is obtained in respect of neutralisation of an odour.

The powder compositions of the invention can be used to remove odours from an ambient atmosphere; in particular these compositions can be present in air-permeable containers, for example bags, so that the atmosphere can permeate into contact with the compositions.

The powder compositions of the invention can be used to remove smells from almost any kind of surface. Thus, for example, they can be shaken over a carpet or other soft-furnishings (curtains, sofas and the like), and later brushed/vacuumed off and collected up. Similarly, they can be spread over a work surface—a kitchen table, for instance—and then wiped off after they have done their work. It is very desirable to apply the powder compositions in containers, for example in the form of bags or pads made of porous materials. There may be surfaces where the odour (of substances such as petroleum spirit and diesel oil) is absorbed deep into the porous material (wood or brick, for instance) from which the surface is made. In such cases it may be desirable, if it is possible, to heat the surface (perhaps to 30–45° C.) and so assist in the evaporation/outgassing of the odour molecules and their subsequent trapping and neutralisation/removal by the powder composition. In some cases, where the source of the smell is permanent—as with a dry toilet, or a pet's litter tray—the powder composition is shaken on and simply left there.

The powder composition of the invention can be associated with a foam-forming carrier substance.

Although for applications to sources such as sludge, pets' litter trays and waste treatment plants the powder compositions of the invention are satisfactory, nevertheless their effect can be improved if they are reformulated into more smell-restraining forms, and particularly foams.

Where a rotting or composting process takes place, volatile gases, such as methane, are formed. The present powder composition interacts with at least some of these volatile gases to bind them. Such gases themselves have little odour, but they carry odour molecules, e.g. sulphides and mercaptans, formed in the process, out into the surrounding air. A dry powder layer on the surface can contribute much to this neutralisation of the odour molecules as they pass through even a very thin dry powder layer on the surface. However, this surface effect can be enhanced if the powder composition is dispersed in a foam layer on the surface. Desirably biodegradable, such a foam containing the powder composition can greatly facilitate the odour neutralisation as it may act as a barrier to the odour molecules (acting as a lid without significantly reducing the access of oxygen); it may also protect the powder composition therein from rainfall and moisture. A good distribution is more easily achieved in this manner.

Accordingly, in an eighth aspect, the present invention provides a method of suppressing odours, wherein an odour-suppressing material in the form of a foam is applied to the source of the odour and wherein the material comprises a foam-form carrier in which is dispersed an odour-suppressing composition according to the invention and active to neutralise the odour.

The powder composition can also be used to remove odours from open air sludge treatment and composting activities as well as for odour removal in closed aerobic and anaerobic reactors.

The toxicity level of the present preferred powder composition has been kept so low that no harm or irritation should come to users whether by inhalation or contact with the skin, even with extensive daily use. However, the alkaline nature of the powder composition (it has a pH of 8.5 in water) makes the employment of dust protection necessary for extensive use. The ingredients are used to a large extent in food products or as additives to farming soil. The composition neutralizes a number of materials that, in addition to generating odours, may cause allergic reactions. Moreover, the composition should not react chemically or otherwise damage constructional material, textiles, plastics, or the like.

The present powder composition is usable in hospitals, homes for elderly people, cars, toilets, boats, tents and caravans, for example.

The treatment of household waste, particularly sewage, and wet organic matter, represents ever-increasing problems in most industrialized countries. Usually, such treatment plants are located in the vicinity of populated regions. Such facilities can be open windrow composting plants or closed reactor systems operated under aerobic or anaerobic conditions. Quite frequently, severe odour problems arise when temperatures and other climatic conditions are unfavourable, or when windrows are turned or opened after long periods generating anaerobic conditions as part of the composting process, or when moved.

In large scale outdoor composting and sludge treatment plants, several odour profiles occur. Amines (fish smell), mercaptans (rotting cabbage), and hydrogen sulphide (rotten eggs) are possibly the most predominant and troublesome components. Considerable methane gas generation also takes place in the plants. Although these gases in themselves may not have strong smells, they often contribute greatly to the spreading of other, much more objectionable odour molecules in the surrounding air. Generally, such plants are of large physical dimensions, and so finding practical solutions to odour problems that can be adapted to the various local conditions and needs is a difficult task. For treatment of off-gassing from closed reactor systems, biofilters and/or wet scrubbers are normally used. The investment and maintenance costs of such systems can be considerable.

Naturally, it is perfectly possible to deal with odours from these sources simply by applying one of the powder compositions of the invention. However, we have found that a particularly advantageous treatment method involves not only such a use of the powder composition but also the spraying into the ambient air around the odour source of an odour-suppressing spray composition, which could be in the form of a powder (even the powder composition of the present invention) or liquid.

In a ninth aspect of the present invention, there is provided a method of suppressing odours from odour-generating solids, comprising applying an odour-suppressing powder composition to said solids and spraying into atmospheric air over said solids an odour-suppressing spray composition.

By this technique, both relatively short-term and relatively long-term suppression of odours emanating from the same solids source can be obtained.

The powder composition and the liquid spray composition of the present invention are particularly suitable for such odour suppression.

Those compositions, moreover, provide the possibility of a flexible approach to such odour problems. When quick action is desirable, the spray composition is better suited. Air-borne odours are usually neutralized within seconds. In outdoor composting plants, and especially during windrow turning operations the air quality improvement can be noticed almost immediately, provided that the spray composition is reasonably well distributed over the areas of the plant where the odour problems are most intense. This can be attained with heavy-duty high-power spray guns.

Odours are generated continuously in such plants, and after spray treatment of the airborne smells, the subsequent generation of smells can be reduced by application of the powder composition, which has an effect over a much longer time interval. The powder composition can also be mixed into the windrows during the turning/aeration process,thus suppressing odours for longer periods while composting or during transport to the end-user. The duration of this effect depends largely on the moisture uptake of the powder composition. The capacity of the powder composition is reduced when the moisture content is high. In many cases, the spray composition can be applied solely, i.e. without use of a powder composition. The spray treatment can be repeated, if desired.

The following Examples and Test Results are now given, though by way of illustration only, to show details of preferred stock formulations, and of the spray compositions prepared therefrom, to show the latter's effectiveness as deodourizers, and to show details of preferred powder compositions and their effectiveness as odour neutralisers.

EXAMPLE I

Stage 1: Preparation of a Stock Formulation I

A stock formulation I was prepared with the following ingredients in the amounts given in Table 1.

TABLE 1

Ingredients, purpose and weight ratios of stock powder formulation I.

| Ingredient Name | Purpose | Formulation I Weight % |
|---|---|---|
| Sodium bicarbonate | amphoteric agent | 60 |
| Sodium sulphate | drying agent (for the stock formulation) | 35 |
| Magnesium sulphate | drying agent and filler | 2.5 |
| Potassium chloride | filler | 2.5 |

All ingredients were sieved through a 1 mm sieve and then mixed in a screw mill.

The stock formulation was stored in a polyethylene bag inside an air- and moisture-tight metal container. The bag was evacuated while inside the container before closing the container with an air-tight lid. The powder has a shelf life of approaching one year under proper storage conditions, without lumps forming.

Stage 2: Preparation of the Spray Composition I

One part by weight of the stock formulation was slowly mixed into 99 parts by weight of normal tap water at 20° C. with agitation. The produced solution was stable but, if it was to be stored for more than one week before use, a preserving compound (such as a water-soluble paraben) was added to suppress microbiological growth.

PRODUCT TESTS

The capacities of the odour neutralising spray were tested against four odour-generating materials, of which two (butyric acid; hydrogen sulphide) were acidic and two (ammonia; n-butylamine) were alkaline. These odour-generating materials are all known to occur frequently in connection with rotting and composting of organic matter, food decay, sewage and sludge.

TEST A—INSTRUMENTAL TEST

The tests were performed in 1.14 L glass bottles.

TEST A PROCEDURE

The odour-generating material samples were introduced onto a filter paper (except for the hydrogen sulphide, which was generated in a small vial) in a 1.14 L glass bottle with a screw lid lined with TEFLON® septa and allowed to equilibrate for approximately 10 minutes before the introduction of the spray composition or of pure water spray. Reference bottles (i.e. those without any spray treatment) and "zero" bottles (i.e. those without the odour-generating materials, but given the spray treatments) were also included. In addition, the bottles were rotated at various intervals to speed up the equilibration process. The spray was administered through 50 ml spray bottles with an average delivery of 110 µl per squirt. A total of 1.1 g of spray composition (10 squirts) was added through the opened bottle.

Instrumental analysis was carried out with a Perkin Elmer Voyager gaschromatograph with a photoionisation detector (GC-PID), used in the Volatile Organic Compound (VOC) mode with syringe sampling through the glass bottle septum and manual injections. The GC-PID is extremely sensitive for volatile acids as well as sulphur- and nitrogen-containing compounds.

Final analysis of the samples was carried out after 30 minutes.

TEST B—OLFACTOMETRIC TEST

In addition to the instrumental tests, simple olfactometric tests were set up using butyric acid, ammonia, and n-butylamine as test substances. The olfactometric test was carried out to evaluate and if possible to confirm the results obtained in the other tests.

TEST B PROCEDURE

A defined amount of odour-generating material was added initially. The spray composition or pure water spray was squirted into sample-containing 120 ml glass bottles with screw lids, using multiple additions through the opened bottle until complete odour neutralisation appeared to be obtained. Olfactometric detection was carried out by opening of the screw lids and judging the "smell" on a scale of 1–10 over periods of up to 5 hours. Capacity evaluations were based on the amount of spray needed to neutralise the odour.

RESULTS AND DISCUSSION

The challenges in performing product tests with a spray are several. This includes the production of reproducible concentrations; introducing the spray uniformly in the volume of air without diluting the sample and taking out and analysing a sample in a reproducible manner.

The effect of an aqueous spray composition is therefore generally more difficult to quantify compared with the effect of odour removal by dry powders. The amount of the active proportion of the spray composition (1% by weight) is small, and thus the difference in odour removal efficiency for different compositions is less evident. Even pure water used as a spray will have an effect partly by contacting and dissolving the odour compounds in the air and partly by acting as "reaction vessels" for natural oxidation processes in the atmosphere with or without the influence of sunlight.

All of the odour-generating materials tested were relatively water-soluble. The odours were chosen from a range of acidic to alkaline and with high to medium polarity and water-solubility. Good removal efficiency would therefore also be expected by use of pure water spray treatments.

The capacity of a spray system for odour removal tabulated in mg odour component per g of spray will be influenced to a large extent by the initial concentration. The same amount of an aerosol spray will "take out" more milligrams of an odour component in a high concentration atmospere compared with low concentration atmospheres.

Table 2 summarises the concentrations used and the results obtained for the TEST A. Results for the TEST B are included in parentheses in the last column of the Table.

TABLE 2

Effect of spray composition for removal of odours

| Odour-Generating Material | Amount of Odour-Generating Material (mg) | Sample concentration in Bottle (mg/m$^3$)/(ppm) | Addition to sample P-spray composition | VOC Response from PID | Relative Decrease (%) | PID Measured Neutralising Capacity (mg/g) (olfact) |
|---|---|---|---|---|---|---|
| Butyric acid | | | | | | |
| Water (200 µl) | 0 | 0/0 | 1.1 g 1% P | 16.4 | — | — |
| Water (200 µl) | 0 | 0/0 | 1.1 g Water | 14.1 | — | — |
| Butyric acid 15%, 200 µl | 30 | 26300/7300 | 1.1 g 1% P | 33.7 | 98 | >26* (3.3) |

TABLE 2-continued

Effect of spray composition for removal of odours

| Odour-Generating Material | Amount of Odour-Generating Material (mg) | Sample concentration in Bottle (mg/m$^3$)/(ppm) | Addition to sample P-spray composition | VOC Response from PID | Relative Decrease (%) | PID Measured Neutralising Capacity (mg/g) (olfact) |
|---|---|---|---|---|---|---|
| Butyric acid 15%, 200 μl | 30 | 26300/7300 | 1.1 g water | 33.4 | 98 | >26 (<2) |
| Butyric acid 15%, 200 μl | 30 | 26300/7300 | no addition | 1606 | 0 | |
| Hydrogen sulphide | | | | | | |
| 140 μl 3M H$_2$SO$_4$ | 0 | 0/0 | 1.1 g 1% P | 3 | — | |
| 140 μl 3M H$_2$SO$_4$ | 0 | 0/0 | 1.1 g Water | 3 | — | |
| 122 mg Na$_2$S (8H$_2$O) + 140 μl 3M H$_2$SO$_4$ | 19 | 16400/12900 | 1.1 g 1% P | 476 | 32 | 5.4 (**) |
| 129 mg Na$_2$S (8H$_2$O) + 140 μl 3M H$_2$SO$_4$ | 20 | 17400/12500 | 1.1 g Water | 615 | 12 | 2.2 |
| 121 mg Na$_2$S (8H$_2$O) + 140 μl 3M H$_2$SO$_4$ | 19 | 16200/11600 | no addition | 701 | 0 | |
| Ammonia | | | | | | |
| Water 100 μl | 0 | 0/0 | 1.1 g 1% P | 9.3 | — | |
| Water 100 μl | 0 | 0/0 | 1.1 g Water | 6.5 | — | |
| Ammonia 2.5% 100 μl | 2.5 | 2200/3150 | 1.1 g 1% P | 85 | 91 | 1.9 (0.5) |
| Ammonia 2.5% 260 μl | 2.5 | 2200/3150 | 1.1 g Water | 118 | 88 | 1.8 (<0.4) |
| Ammonia 2.5% 260 μl | 2.5 | 2200/3150 | no addition | 923 | 0 | |
| n-Butylamine | | | | | | |
| Water 100 μl | 0 | 0 | 1.1 g 1% P | 526 | — | |
| Water 100 μl | 0 | 0 | 1.1 g Water | 361 | — | |
| n-Butylamine 2.5% 100 μl | 2.5 | 2200/735 | 1.1 g 1% P | 850 | 65 | 1.1 (0.6) |
| n-Butylamine 2.5% 100 μl | 2.5 | 2200/735 | no addition | 2305 | 0 | |
| n-Butylamine 2.5% 100 μl | 2.5 | 2200/735 | 1.1 g Water | 809 | 65 | 1.1 (<0.3) |

*Theoretical value - 6.6 mg/g
**Not measured

The olfactometric test results in Table 2 show that generally lower capacity numbers were found in these tests which were performed at lower concentrations compared with the instrumental testing. The capacities found were for buryric acid 3.3 mg/g, for ammonia 0.5 mg/g and for n-butylamine 0.6 mg/g for the spray composition. For all of the odour components a better performance was found for the spray composition in comparison with the water spray. The test for butyric acid was the most convincing test and confirmed that the spray composition is efficient for bytyric acid removal. The uncertainties in these numbers should be considered higher as compared with instrumental tests. If an equilibrium model is applied, lower capacity numbers should be expected with lower olfactometric detection threshold values. The detection limit for the human nose is several decades lower than the GC-PID detection limits for the same gases.

In cases where a relative decrease of 95% or more was reached, the capacity is tabulated as greater than (>). The spray composition was found to act quickly in all cases, and the GC-PID instrument tests were therefore limited to 30 minutes duration. Such small addition of spray solution meant that a considerable odour was evident in the bottles after finishing the instrumental tests. Although indicative of the capacity in odour gas neutralisation per unit weight of spray, it is difficult to judge to what extent the odour can be completely removed (reduced to levels below human odour detection thresholds), when measuring at these high concentrations of odour-generating material.

The theoretical capacity for butyric acid based on the alkaline nature of the spray should be about 6 mg/g of spray. The effect in the instrumental test was found to be >26 mg/g with a 98% removal efficiency. The same capcaity was found for pure water spray. This indicates that the removal of butyric acid in this case and at this concentration can be attributed to the water effect. The effects found were in the 3–27 mg/g range. The olfactometric test made on the spray composition for butyric acid did show considerably higher neutralisation capacity of the spray composition compared with the pure water aerosol spray. (One of the most simple tests is to compare water and the spray composition as a washing solution for the removal of butyric acid on the skin. The spray composition gives far better results).

The instrumental removal capacity for hydrogen sulphide was found to be 5.4 mg/g (32% removal) compared with 2.2 mg/g (12% removal) for pure water spray. This indicated a 2.5 times better capacity for the spray composition. The concentration levels after exposure to the spray composition are still high compared with the human odour threshold values.

The instrumentally measured removal capacity for ammonia was found to be 1.9 mg/g for the spray composition (91% removal) and 1.8 mg/g for the water spray (88% removal). This is hardly a significant difference, implying that the water effect is the dominating factor in the removal capacity. The olfactometric test revealed that the remaining odour in the bottle treated with the spray composition was much lower compared with the bottle treated with pure water spray. The reason for this may be that the human nose detection threshold for ammonia is high (about 17 ppm) compared to the other odour molecules tested. This means that the nose may be better than an instrument in detecting small differences in removal capacity.

For n-butylamine, the instrumental removal capacity was found to be about 1.1 mg/g for the spray composition (65% removal) and 1.1 mg/g for the pure water spray (65% removal). No difference in efficiency was therefore found. This capacity was at a similar level as found for ammonia and low compared with the capacities for the acidic odour-generating materials tested above.

The capacity of the spray composition in relation to odour molecules seems to be difficult to distinguish from the effect of pure water spray, at least at the high concentrations necessary to do instrumental analysis. An exception to this is the hydrogen sulphide test where the spray composition was found to be 2.5 times more efficient compared with water.

At lower concentrations, there is a clear indication using simple olfactometric evaluations that the spray composition also reacts chemically with odour molecules, thus neutralising and removing such molecules efficiently.

CONCLUSIONS

All of the odour-generating materials tested were water-soluble. The compounds tested were representatives of different odour compounds found during decay of organic matter in various conditions such as rotting and composting. High removal efficiency would therefore also be expected by use of pure water spray treatments. The tests have shown that this is indeed the case. Only for hydrogen sulphide was a significantly higher removal efficiency found for the spray composition compared with pure water spray in the instrumental tests. The spray composition was found to perform better when compared with the water spray for butyric acid, ammonia and n-butylamine.

The instrumental tests were performed at higher concentration levels compared with the olfactometric tests. Even after an instrumentally-recorded decrease of 98% in the odour, hardly any difference in the smell is likely to be detected by the nose, compared with the reference sample with pure water spray. The reason is that, even after such a reduction in the smell in a bottle, the odour level might still be one million times higher than the nose detection thresholds.

It is indeed surprising that a water-based spray composition with sodium bicarbonate as the main active ingredient could be this effective. The odour neutralisation effect of the stock formulation is greatly reduced by adding moisture. The stock formulation powder is hygroscopic and the formation of lumps as moisture content increases, reduces the active surfaces of the powder. This has probably deterred people from experimenting with powders dissolved in water and applied as a spray. In the latter case only very small amounts of active material can be distributed. However, since the odour molecules are very small and occur in low concentrations, only minute amounts of active material are required to neutralise them. It thus seems more a question of good distribution of the active material in the air and on surfaces to neutralise the widely spaced odour molecules. This observation has possibly been difficult to verify, partly owing to the rather strong, immediate, odour reduction of pure water sprays. The differences between pure water spray and the spray composition are, according to our observations, often mainly evident at rather low odour levels, and determinable by olfactometric methods.

EXAMPLE II

Stage 1: Preparation of a Stock Formulation II

A stock formulation II substantially the same as in Example I was prepared with the following ingredients in the amounts given in Table 3.

TABLE 3

Ingredients, purpose and weight ratios of stock powder formulation II.

| Ingredient Name | Purpose | Formulation II Weight % |
|---|---|---|
| Sodium bicarbonate | amphoteric agent | 60 |
| Sodium sulphate | drying agent (for the stock formulation) | 30 |
| Magnesium sulphate | drying agent and filler | 5 |
| Potassium chloride | filler | 5 |

All ingredients were sieved through a 1 mm sieve and then mixed in a screw mill.

The stock formulation was stored in a polyethylene bag inside an air- and moisture-tight metal container. The bag was evacuated while inside the container before closing the container with an air-tight lid. The powder has a shelf life of approaching one year under proper storage conditions, without lumps forming.

Stage 2: Preparation of the Spray Compositions II 1 to 5 parts by weight of the stock formulation was slowly mixed into 95 to 99 parts by weight of normal tap water at 20° C. with agitation to produce spray compositions with end product concentrations of 1–5%. The produced solutions were stable but, if they were to be stored for more than one week before use, preserving compounds, Nipagin-M-Sodium ($C_8H_7NaO_3$) (0.4% by weight) and Nipasol-M-Sodium ($C_{10}H_{11}NaO_3$) (0.15% by weight) were added to suppress microbiological growth.

The test results obtained using the spray compositions II were substantially the same as those using the spray composition I.

When the formulations I and II are 1.5% concentrations in their spray compositions, they are isotonic relative to human body fluids.

EXAMPLE III

Stage 1: Preparation of a Stock Formulation III

A stock formulation III was prepared with the following ingredients in the amounts given in Table 4.

TABLE 4

Ingredients, purpose and weight ratios of stock powder formulation III.

| Ingredient Name | Purpose | Formulation II Weight % |
|---|---|---|
| Sodium bicarbonate | amphoteric agent | 61 |
| Magnesium sulphate | drying agent and filler | 9 |
| α Cyclodextrin | organic complexing agent | 10 |
| β Cyclodextrin | organic complexing agent | 10 |
| γ Cyclodextrin | organic complexing agent | 10 |

All ingredients were sieved through a 1 mm sieve and then mixed in a screw mill.

The stock formulation was stored in a polyethylene bag inside an air- and moisture-tight metal container. The bag was evacuated while inside the container before closing the container with an air-tight lid. The powder has a shelf life of approaching one year under proper storage conditions, without lumps forming.

Stage 2: Preparation of the Spray Composition III

One part by weight of the stock formulation was slowly mixed into 99 parts by weight of deionized and distilled water at 20° C. with agitation to produce a spray composition with an end product concentration of 0.8%. The produced solution was stable but, if it was to be stored for more than one day before use, a preserving compound, Kathon CG, was added in amounts of between 7–20 ppm (0.0007–0.002%), to suppress microbiological growth.

This spray composition III was particularly useful in removing odours from textiles upon which it was sprayed.

EXAMPLE IV

Stage 1: Preparation of a Stock Formulation IV

A stock formulation IV was prepared with the following ingredients in the amounts given in Table 5.

TABLE 5

Ingredients, purpose and weight ratios of stock powder formulation IV.

| Ingredient Name | Purpose | Formulation IV Weight % |
| --- | --- | --- |
| Sodium bicarbonate | amphoteric agent | 88 |
| Sodium sulphate | drying agent (for the stock formulation) | 2.2 |
| Magnesium sulphate | drying agent and filler | 2.2 |
| Potassium chloride | filler | 2.2 |
| Lauryl sulphate | surfactant | 2.2 |
| Miranol Ultra | surfactant | 1.6 |
| Brij 35 | surfactant | 0.8 |
| Tween 40 | surfactant | 0.8 |

All dry ingredients were sieved through a 1 mm sieve and then mixed in a screw mill.

The stock formulation was stored in a polyethylene bag inside an air- and moisture-tight metal container. The bag was evacuated while inside the container before closing the container with an air-tight lid. The powder has a shelf life of approaching one year under proper storage conditions, without lumps forming.

Stage 2: Preparation of a Concentrate from Formulation IV 8.6 parts by weight of the inorganic ingredients of the dry powder formulation was added to 85.9 parts of distilled or deionized water with mixing for a few hours. At the same time 0.5 parts of the organic surfactants was added to 5 parts of distilled or deionized water with thorough mixing. The mixture of organic surfactants and water was then added to the mixture of inorganic ingredients and water to produce a 10% concentrate. The solution was stable but, if it was to be stored for more than one day before use, a preserving compound, Suttocide ($C_5H_7NO_3Na^+$), was added in an amount of 1% by weight, to suppress microbiological growth.

Stage 3: Dilution of the Concentrate

So that the concentrate could be safely used, it was diluted by mixing 1 part concentrate to 100 parts water to produce a 0.% concentration.

This spray composition was particularly useful in removing odours produced by compost.

EXAMPLE V

Preparation of Powder Compositions

Three kinds of powder compositions, each kind consisting of two differing compositions, were prepared with the following ingredients in the amounts given in Table 6.

TABLE 6

Ingredients, purpose and weight ratios of powder compositions.

| | | | Weight % (*) | | | | | |
| | | | Comp. I | | Comp. II | | Comp. III | |
| Name | Formula | Purpose | A | B | A | B | A | B |
| --- | --- | --- | --- | --- | --- | --- | --- | --- |
| Sodium bicarbonate | $NaHCO_3$ | Amphoteric agent | 83 | 85 | 83 | 85 | 50 | 51 |
| Zinc oxide | ZnO | Amphoteric agent | | | | | 33 | 34 |
| Ferrous sulphate | $FeSO_4$ | Ammonia/sulphide remover | 3 | | | | 3 | |
| Ferrous sulphate heptahydrate | $FeSO_4 *7H_2O$ | Ammonia/sulphide remover | | 5 | | | | 5 |
| Zinc sulphate monohydrate | $ZnSO_4 *H_2O$ | Ammonia/sulphide remover | | | 3 | | | |
| Zinc sulphate heptahydrate | $ZnSO_4 *7H_2O$ | Ammonia/sulphide remover | | | | 5 | | |
| Sodium sulphate | $Na_2SO_4$ | Drying agent | 7 | 7 | 7 | 7 | 7 | 7 |
| Zeolite (Clinoptilolite) | $M_2/ n*Al_2O_3* ySiO_2 *wH_2O$ | Adsorbent | 5 | 5 | 5 | 5 | 5 | 5 |

In respect of ferrous sulphate, zinc sulphate and zeolite in the A and B compositions, there were different contents of crystal water associated with the metal.

All ingredients were sieved through a 1 mm sieve and then mixed in a screw mill. The powder dust settled within 10–15 seconds (as observed by visual inspection) after shaking a sample in a quarter-filled bottle.

Comp. I was a powder with a greenish/beige colour when freshly made, turning slightly red/brown because of iron oxidation. Comp. II was a version of Comp. I with zinc sulphate instead of iron sulphate. This meant that no oxidation took place and the powder stayed white or greyish/white. This is important for uses where the possibility of leaving stains after use of the composition must be avoided. When the Comp. II powders were to be stored in air-tight plastics bags zinc sulphate heptahydrate was avoided because of $CO_2$ liberation at relatively low temperatures (starting at about 30° C.). Comp. III was a version where the main ingredient was partly replaced by another amphoteric compound.

Except for Composition IIA, each composition was stored in a polyethylene bag inside an air- and moisture-tight metal container. The bag was evacuated while inside the container before closing the container with an air- and moisture-tight lid.

Each powder composition has a shelf life of approaching one year under proper storage conditions, without lumps forming.

The different powder compositions were tested against four different odour components as described below.

TEST C

The capacities of each of the powder compositions IA, IIA and IIIA to neutralise odours were tested against four different odour-generating materials; butyric acid, hydrogen sulphide, ammonia and n-butylamine (or triethylamine). These odour-generating materials are all known to occur frequently in connection with rotting and composting of organic matter, food decay, sewage and sludge.

The thus formed powder compositions were tested in the following manner.

TEST C PROCEDURE

The odour-generating materials (except for hydrogen sulphide which was generated in situ by adding sulphuric acid to solid sodium sulphide) were used in concentrated form (butyric acid, triethylamine) or as diluted water samples (ammonia 25%, n-butylamine 20%) in amounts given in Tables 7, 8 and 9. The odour components were introduced into 1.14 liter sample bottles, with screw lids lined with TEFLON® septa. The samples were carried in the bottles by pieces of filter paper (except for hydrogen sulphide, which was kept in a small vial in the bottle), so as to absorb any water and allow better equilibration of the odour-generating material in the bottles. Reference bottles (i.e. those without the powder composition) and "zero" bottles (i.e. those without the odour-generating material) were prepared. The bottles were rotated at various intervals to speed up the equilibration process in the relevant bottles.

Deodourising powder compositions IA, IIA, and IIIA were added in the amounts given in Tables 7, 8 and 9. Instrumental analysis was carried out with a Perkin Elmer Voyager gaschromatograph with a photoionisation detector (GC-PID), used in the Volatile Organic Compound (VOC) mode with syringe sampling through the bottle septum and manual GC injections. The GC-PID is extremely sensitive for volatile acids as well as sulphur- and nitrogen-containing compounds. Final analyses of most of the samples were carried out after 24 hours, but for other samples after 48 hours.

The make-up of the samples and the analytical results are summarised in Tables 7, 8 and 9.

TABLE 7

Effect of powder composition IA in removal of odours

| Odour-Generating Material | Amount of Odour-Generating Material (mg) | Sample Concentration in Bottle $(mg/m^3)$/(ppm) | Amount of Deodourising Powder in Sample (g) | VOC Response from PID | Relative Decrease (%) | PID Measured Neutralising Capacity (mg/g) |
|---|---|---|---|---|---|---|
| Butyric acid | | | | | | |
| Nothing (dry filter paper) | 0 | 0/0 | 0.55 | 2 | — | — |
| Conc. Butyric acid 500 µl | 480 | 420000/117000 | 0.52 | 287 | 70 | 700 |
| Conc. Butyric acid 500 µl | 480 | 420000/117000 | 0.00 | 996 | 0 | 0 |
| Hydrogen sulphide* | | | | | | |
| 3M $H_2SO_4$ 500 µl | 0 | 0/0 | 1.00 | 15 | — | — |
| $Na_2S$ 365 mg + 3M $H_2SO_4$ 500 µl | 56 | 49100/35000 | 1.00 | 17 | 100 | >56 |
| $Na_2S$ 347 mg + 3M $H_2SO_4$ 500 µl | 53 | 46500/33000 | 0.00 | 7318 | 0 | 0 |
| Ammonia | | | | | | |
| Water 260 µl | 0 | 0/0 | 2.03 | 1 | — | — |
| Ammonia 25% 260 µl | 59 | 52000/74600 | 2.02 | 82 | 90 | 30 |
| Ammonia 25% 260 µl | 59 | 52000/74600 | 0.00 | 676 | 0 | 0 |
| n-Butylamine | | | | | | |
| Water 165 µl | 0 | 0/0 | 2.52 | 3 | — | — |
| n-Butylamine 20% 165 µl | 33 | 29000/9700 | 2.51 | 68 | 94 | 12 |
| n-Butylamine 20% 165 µl | 33 | 29000/9700 | 0.00 | 1055 | 0 | 0 |

*48 h test. The sodium sulphide contained approximately 8 crystal water molecules.

TABLE 8

Effect of powder composition IIA in removal of odours

| Odour-Generating Material | Amount of Odour-Generating Material (mg) | Sample Concentration in Bottle $(mg/m^3)$/(ppm) | Amount of Deodourising Powder in Sample (g) | VOC Response from PID | Relative Decrease (%) | PID Measured Neutralising Capacity (mg/g) |
|---|---|---|---|---|---|---|
| Butyric acid | | | | | | |
| Nothing (dry filter paper) | 0 | 0/0 | 0.50 | 46 | — | — |
| Conc. Butyric acid 500 µl | 480 | 420000/117000 | 0.52 | 289 | 50 | 465 |
| Conc. Butyric acid 500 µl | 480 | 420000/117000 | 0.00 | 594 | 0 | 0 |

TABLE 8-continued

Effect of powder composition IIA in removal of odours

| Odour-Generating Material | Amount of Odour-Generating Material (mg) | Sample Concentration in Bottle $(mg/m^3)$/(ppm) | Amount of Deodourising Powder in Sample (g) | VOC Response from PID | Relative Decrease (%) | PID Measured Neutralising Capacity (mg/g) |
|---|---|---|---|---|---|---|
| Hydrogen sulphide* | | | | | | |
| 3M $H_2SO_4$ 700 µl | 0 | 0/0 | 1.06 | 20 | — | — |
| $Na_2S$ 514 mg + 3M $H_2SO_4$ 700 µl | 79 | 69000/50000 | 1.04 | 8405 | 30 | 23 |
| $Na_2S$ 512 mg + 3M $H_2SO_4$ 700 µl | 79 | 69000/50000 | 0.00 | 11865 | 0 | 0 |
| Ammonia | | | | | | |
| Water 100 µl | 0 | 0/0 | 1.12 | 10 | — | — |
| Ammonia 25% 1000 µl | 225 | 197000/283000 | 1.06 | 45337 | 25 | 53 |
| Ammonia 25% 1000 µl | 225 | 197000/283000 | 0.00 | 60086 | 0 | 0 |
| Triethylamine | | | | | | |
| Nothing (dry filter paper) | 0 | 0/0 | 1.06 | 82 | — | — |
| Conc. Triethylamine 345 µl | 250 | 220000/53000 | 1.05 | 2957 | 10 | 25 |
| Conc. Triethylamine 345 µl | 250 | 220000/53000 | 0.00 | 3304 | 0 | 0 |

*The sodium sulphide contained approximately 8 crystal water molecules.

TABLE 9

Effect of powder composition IIIA in removal of odours

| Odour-Generating Material | Amount of Odour-Generating Material (mg) | Concentration in Bottle $(mg/m^3)$/(ppm) | Amount of Deodourising Powder in Sample (g) | VOC Response from PID | Relative Decrease (%) | PID Measured Neutralising Capacity (mg/g) |
|---|---|---|---|---|---|---|
| Butyric acid | | | | | | |
| Nothing (dry filter paper) | 0 | 0/0 | 0.50 | 46 | — | — |
| Conc. Butyric acid 500 µl | 480 | 420000/117000 | 0.54 | 383 | 35 | 310 |
| Conc. Butyric acid 500 µl | 480 | 420000/117000 | 0.00 | 594 | 0 | 0 |
| Hydrogen Sulphide* | | | | | | |
| 3M $H_2SO_4$ 700 µl | 0 | 0/0 | 1.06 | 20 | — | — |
| $Na_2S$ 500 mg + 3M $H_2SO_4$ 700 µl | 79 | 69000/50000 | 1.03 | 4824 | 60 | 47 |
| $Na_2S$ 500 mg + 3M $H_2SO_4$ 700 µl | 79 | 69000/50000 | 0.00 | 11865 | 0 | 0 |
| Ammonia | | | | | | |
| Water 1000 µl | 0 | 0/0 | 1.12 | 10 | — | — |
| Ammonia 25% 1000 µl | 225 | 197000/283000 | 1.04 | 37532 | 38 | 82 |
| Ammonia 25% 1000 µl | 225 | 197000/283000 | 0.00 | 60086 | 0 | 0 |
| Triethylamine | | | | | | |
| Nothing (dry filter paper) | 0 | 0/0 | 1.06 | 82 | — | — |
| Conc. Triethylamine 345 µl | 250 | 220000/53000 | 1.03 | 5339 | 0 | 0 |
| Conc. Triethylamine 345 µl | 250 | 220000/53000 | 0.00 | 3304 | 0 | 0 |

*The sodium sulphide contained approximately 8 crystal water molecules.

TEST D

In addition to the instrumental tests simple olfactometric tests were carried out with butyric acid and ammonia on composition IA.

TEST D PROCEDURE

To each sample bottle 1.0 g of dry deodourising powder was added in each test. The diluted odour-generating materials were sprayed into 120 ml glass powder-containing bottles with a screw lid using multiple additions through the opened bottle until complete odour neutralisation appeared to be obtained. Olfactometric detection was carried out by opening of the screw lids and judging the "smell" on a scale of 1–10 over periods of up to 80 hours.

TEST D RESULTS

The simple olfactometric tests revealed a capacity of about 900 mg/g for butyric acid and 3.5 mg/g for ammonia.

TEST E

In order to test for any synergistic effect of the compositions compared with the odour-neutralising effects of their respective ingredients in relation to the four odours in question, the individual ingredients in the form of powders were subjected to a test similar to test C. The results thereof are presented in Table 10.

TABLE 10

Odour-removal effect of ingredient powders

| Powder sample | PID Measured Neutralising Capacity (mg/g) |
|---|---|
| Butyric acid | |
| Sodium bicarbonate | 680 |
| Zinc oxide | 465 |
| Iron sulphate heptahydrate | 470 |
| Zinc sulphate heptahydrate | 0 |
| Sodium sulphate | 400 |
| Zeolite | 410 |
| No powder | 0 |
| Hydrogen sulphide | 24 h/48 h |
| Sodium bicarbonate | 82/58 |
| Zinc oxide | 80 |
| Iron sulphate heptahydrate | 80/0 |
| Zinc sulphate heptahydrate | 25 |
| Sodium sulphate | 24/0 |
| Zeolite | 27/16 |
| No powder | 0 |
| Ammonia | |
| Sodium bicarbonate | 2 |
| Zinc oxide | 12 |
| Iron sulphate heptahydrate | 126* |
| Zinc sulphate heptahydrate | >30 |
| Sodium sulphate | 0 |
| Zeolite | 12 |
| No powder | 0 |
| n-Butylamine/triethylamine | 24 h/48 h |
| Sodium bicarbonate | 11/– |
| Zinc oxide | –/0 |
| Iron sulphate heptahydrate | 13/– |
| Zinc sulphate heptahydrate | >5/– |
| Zeolite | 11/– |
| No powder | 0 |

*Calculated

DISCUSSION OF RESULTS

The odour gas neutralisation capacities measured by the Perkin Elmer GC-PID instrument were somewhat higher than some indicative results performed by simple olfactometric tests. The difficulties in setting up repeatable, controlled experiments and the fact that the instrumental tests and the olfactometric tests had to be conducted at very different concentration levels must be taken into consideration when comparing results from different tests and when comparing compositions. In samples where a relative decrease of 95% or more was reached, the capacity was tabulated as greater than (>).

The capacity of the powder compositions for odour neutralisation of acidic compounds (butyric acid) was quite striking. This was the case for all of the three powder compositions tested (300–700 mg/g). Many organic lipid-containing materials produce organic acids as products during natural decay and composting processes. This effect is therefore a valuable one to give a long-term effect of powders for odour control during decay of organic compounds. The capacity of composition IA for removal of butyric acid is high compared with a theorectical value (380 mg) based on a 1:1 reaction on the molecular level, and on the amount of sodium bicarbonate present. This indicated adsorption effects in addition to the neutralisation capacity. The other powder compositions also performed reasonably well in respect of butyric acid. The efficiency seems to be proportional to the amount of sodium bicarbonate in the composition. As can be seen from Table 10, the efficiency of each ingredient was highest for sodium bicarbonate followed by zinc oxide and zeolite. No specific synergistic effects were found. Potassium bicarbonate and zinc oxide (ZI 105; SvedaKjemi) were tested as alternatives to sodium bicarbonate and were found to give comparable removal efficiencies (both showing capacities of about 700 mg/g).

A significant effect for removal of hydrogen sulphide, another acidic compound, was found especially in the iron-containing powders (>56 mg/g for composition IA and 47 mg/g for composition IIIA). In the case of composition IA a synergistic (more than additive) effect of at least 2 times was found for the powder composition compared with the composition ingredients. This effect is probably higher, but the composition IA was not tested to the limit of its capacity in respect of hydrogen sulphide. The best effects for the composition ingredients were found for sodium bicarbonate, for zinc oxide and for ferrous sulphate heptahydrate. Reactions between ferrous iron and sulphide took place in addition to acid/alkaline neutralisation reactions. Ferric salts, i.e. the oxidised form of ferrous iron, were also found to be effective which means that good removal efficiencies for sulphides even after oxidation of the iron in the powder composition to the red/brown rusty colour are expected. Zinc sulphate (heptahydrate) was found to be a good replacement for iron sulphate in the powder composition if a white powder composition is required. The capacity for this substance was found to be >10 mg/g. The most effective hydrogen sulphide remover found was zinc oxide (ZI 0855; SvedaKjemi) at a capacity of 30 mg/g or above. This is reflected in the rather high capacity of composition IIIA for hydrogen sulphide removal (47 mg/g).

The powder compositions also had a significant and unexpected removal capacity for the alkaline odour components ammonia and organic amines. The explanation for this is probably a combination of adsorption, complex formation and the amphoteric nature of the main ingredient.

In the case of ammonia the capacities of the three powder compositions were in the range from 30 to 82 mg/g. The main ingredient responsible for this capacity in the compositions IA and IIIA was found to be ferrous sulphate which indicated a complex formation type of mechanism. Ferric sulphate again was found to be at least as efficient as the ferrous sulphate (>195 mg/g and about 120 mg/g respectively). Oxidation of the powder composition during storage and use will therefore not be a serious problem in relation to ammonia removal. Zinc sulphate was also found to be efficient (>30 mg/g) which indicates again that this is a possible replacement candidate for the iron compounds in the composition.

Zinc oxide was also found to work reasonably well for the removal of ammonia (12–54 mg/g). This is probably the reason why the composition IIIA is the powder composition best suited to deal with ammonia odours. There is also a clear indication that the adsorption effect is significant in this case, as demonstrated by the rather high capacity of the zeolite (12 mg/g).

Organic amines such as n-butylamine and triethylamine (fishy smell) are also removed to some extent by the powder compositions except for the composition IIIA where no significant reduction was noted. These compounds are quite different from the other compounds, as they are less water soluble and alkaline. The odour threshold concentrations of these compounds are very low. The concentrations causing problems in surrounding air are therefore low and the capacity needed to remove bad odours is modest. The same applies for hydrogen sulphide. The best capacity for amines was obtained with the composition IIA (25 mg/g). Typically the best single compounds for removal of these smells were adsorbents (amorphous silica and zeolite) and complexing agents (ferrous and ferric iron and zinc salts).

To summarise, composition IA is the best composition to deal with butyric acid odours. The best composition to deal with organic amines seems to be composition IIA, while composition IIIA is the best composition for ammonia removal.

What is claimed is:

1. A method of neutralizing odor causing molecules, which comprises spraying a composition comprising a large proportion of liquid and a small proportion of a formulation dissolved in said liquid, wherein said formulation comprises an amphoteric material.

2. The method according to claim 1, wherein spraying said composition further comprises spraying said composition as an aerosol.

3. The method according to claim 2, spraying said composition further comprises spraying said composition into the atmosphere to neutralize odor molecules therein.

4. The method according to claim 1, wherein spraying said composition further comprises spraying said composition on wounds, and further wherein said spray composition is an isotonic composition relative to a human body fluid.

5. The method of claim 1, wherein said composition further comprises a drying agent, and wherein said liquid is water and said amphoteric material is a major ingredient of said formulation.

6. The method of claim 1, wherein said composition further comprises a deodorizing agent that is non-toxic and non-oxidizing, and further wherein said spray composition is a solution, said deodorizing agent comprising less than 2% of said composition's total weight, and said amphoteric material is a major ingredient of said formulation and neutralizes odor molecules.

7. The method of claim 1, wherein said formulation further comprises an organic complexing agent and said composition is free of masking agents.

8. The method according to claim 7, wherein spraying said composition further comprises spraying said composition on a textile material to neutralize odors thereat.

* * * * *

UNITED STATES PATENT AND TRADEMARK OFFICE
CERTIFICATE OF CORRECTION

| | |
|---|---|
| PATENT NO. | : 6,703,010 B1 |
| APPLICATION NO. | : 09/831936 |
| DATED | : March 9, 2004 |
| INVENTOR(S) | : Jan Frismark et al. |

It is certified that error appears in the above-identified patent and that said Letters Patent is hereby corrected as shown below:

On the title page insert item [73], Assignee Sanodor AS, a corporation of Norway Signed and Sealed this Twenty-second Day of May, 2007

JON W. DUDAS
*Director of the United States Patent and Trademark Office*